(12) United States Patent
Stahurski

(10) Patent No.: US 6,682,529 B2
(45) Date of Patent: Jan. 27, 2004

(54) CONNECTOR ASSEMBLY WITH MULTIDIMENSIONAL ACCOMMODATION AND ASSOCIATED METHOD

(75) Inventor: Terrence M. Stahurski, Seven Hills, OH (US)

(73) Assignee: Stahurski Consulting, Inc., Seven Hills, OH (US)

( * ) Notice: Subject to any disclaimer, the term of this patent is extended or adjusted under 35 U.S.C. 154(b) by 0 days.

(21) Appl. No.: 10/167,111

(22) Filed: Jun. 11, 2002

(65) Prior Publication Data

US 2003/0229345 A1 Dec. 11, 2003

(51) Int. Cl.[7] .............................................. A61B 17/56
(52) U.S. Cl. ........................................ 606/61; 606/73
(58) Field of Search .............................. 606/60, 61, 71, 606/72, 73

(56) References Cited

U.S. PATENT DOCUMENTS

| | | | | |
|---|---|---|---|---|
| 5,380,326 A | * | 1/1995 | Lin | 606/61 |
| 5,474,551 A | * | 12/1995 | Finn et al. | 606/61 |
| 5,478,340 A | * | 12/1995 | Kluger | 606/61 |
| 5,480,401 A | * | 1/1996 | Navas | 606/61 |
| 5,540,688 A | * | 7/1996 | Navas | 606/61 |
| 5,562,737 A | * | 10/1996 | Graf | 623/17.14 |
| 5,693,053 A | * | 12/1997 | Estes | 606/61 |
| 5,800,435 A | * | 9/1998 | Errico et al. | 606/61 |
| 5,976,135 A | | 11/1999 | Sherman et al. | |
| 6,063,089 A | | 5/2000 | Errico et al. | |
| 6,309,390 B1 | * | 10/2001 | Le Couedic et al. | 606/61 |
| 6,520,990 B1 | * | 2/2003 | Ray | 623/17.11 |
| 6,551,318 B1 | * | 4/2003 | Stahurski | 606/61 |
| 2003/0045879 A1 | * | 3/2003 | Minfelde et al. | 606/61 |

* cited by examiner

Primary Examiner—Pedro Philogene
Assistant Examiner—David A Bonderer
(74) Attorney, Agent, or Firm—Pearne & Gordon LLP

(57) ABSTRACT

A connection assembly connects a bone engaging fastener to an elongate member. In one example, the assembly includes a fastener connector that has two integrally formed portions. The first fastener connector portion is for location adjacent to the bone and has an opening through which the fastener can extend and into the bone. The second fastener connector portion has one part of a ball and socket connection. The assembly includes a member connector that has two integrally formed portions. The first member connector portion has another part of the ball and socket connection engaged with the part of the ball and socket connection of the fastener connector. The second member connector portion has an aperture for receiving the elongate member. In a specific example, the opening in the fastener connector is an elongate slot. An associated method is used to connect the bone engaging fastener to the elongate member.

23 Claims, 3 Drawing Sheets

US 6,682,529 B2

CONNECTOR ASSEMBLY WITH MULTIDIMENSIONAL ACCOMMODATION AND ASSOCIATED METHOD

FIELD OF THE INVENTION

The present invention relates to bone (e.g., spinal) fixation arrangements, and is particularly directed to an assembly and an associated method, for a fixation arrangement, that provides a high degree of adjustment for accommodation along multiple axes in multiple directions.

BACKGROUND OF THE INVENTION

Bone fixation arrangements are used to hold bones or bone pieces. One specific example of a bone fixation arrangement is used for spinal vertebrae fixation and is commonly referred to as a spinal implant. Such spinal implants are used in treatment of patients with deformed and/or mechanically insufficient spinal columns.

Longitudinal members (e.g., rods) of the implant arrangement are typically contoured to a desired configuration and connected to spinal vertebrae via the use of a plurality of connector assemblies and associated bone screws.

Difficulty may be encountered during connection of the implant arrangement to the spinal column. Specifically, insertion of screws along a non-aligned curvature may prove difficult and require increased operating time for placement of an implant arrangement.

SUMMARY OF THE INVENTION

In accordance with one aspect, the present invention provides a connection assembly for connecting a bone engaging fastener to an elongate member. The assembly includes a fastener connector having a slot through which the fastener can extend to secure the fastener connector and the fastener together. The slot is elongate to permit securing of the fastener at any of several locations along the slot. The assembly includes a member connector having a portion to connect with the elongate member. The fastener connector and the member connector have portions that engage each other to permit relative adjustment movement in at least two dimensions and to secure the member connector relative to the fastener connector subsequent to the adjustment.

In accordance with another aspect, the present invention provides a connection assembly for connecting a bone engaging fastener to an elongate member. The assembly includes a fastener connector having a slot through which the fastener can extend to secure the fastener connector and the fastener together. The slot is elongate to permit securing of the fastener to any of several locations along the slot. The assembly includes a member connector having a portion to connect with the elongate member. The fastener connector and the member connector have a universal pivot interconnection there between to permit relative universal pivot adjustment movement.

In accordance with yet another aspect, the present invention provides a connection assembly for connecting a bone engaging fastener to an elongate member. The assembly includes a fastener connector that has two integrally formed portions. The first fastener connector portion is for location adjacent to the bone and has an opening through which the fastener can extend and into the bone. The second fastener connector portion has one part of a ball and socket connection. The assembly includes a member connector that has two integrally formed portions. The first member connector portion has another part of the ball and socket connection engaged with the part of the ball and socket connection of the fastener connector. The second member connector portion has an aperture for receiving the elongate member.

In accordance with still another aspect, the present invention provides a method of connecting a bone engaging fastener to an elongate member. A fastener connector is connected to the bone engaging fastener. The fastener connector has a first fastener connector portion for location adjacent to the bone and that has an opening through which the fastener can extend and into the bone. A second fastener connector portion has a part to engage a member connector. The step of connecting the fastener connector includes selecting a distance, to space the second fastener connector portion from the bone engaging fastener, from among a plurality of distance choices, and securing the fastener connector to the bone engaging fastener with the second fastener connector portion at the selected distance from the bone engaging fastener. The method includes connecting and securing a member connector, which has a portion to connect with the elongate member, to the elongate member. The method includes connecting the fastener connector and the member connector. The fastener connector and the member connector have parts that engage each other to permit relative adjustment movement in at least two dimensions and to secure the member connector relative to the fastener connector subsequent to the adjustment. The step of connecting the fastener connector and the member connector includes relatively adjusting the fastener connector and the member connector in the at least two dimensions and securing the member connector relative to the fastener connector subsequent to the adjustment.

BRIEF DESCRIPTION OF THE DRAWINGS

The foregoing and other features and advantages of the present invention will become apparent to those skilled in the art to which the present invention relates upon reading the following description with reference to the accompanying drawings wherein.

DESCRIPTION OF EXAMPLE EMBODIMENTS

Figure 1:
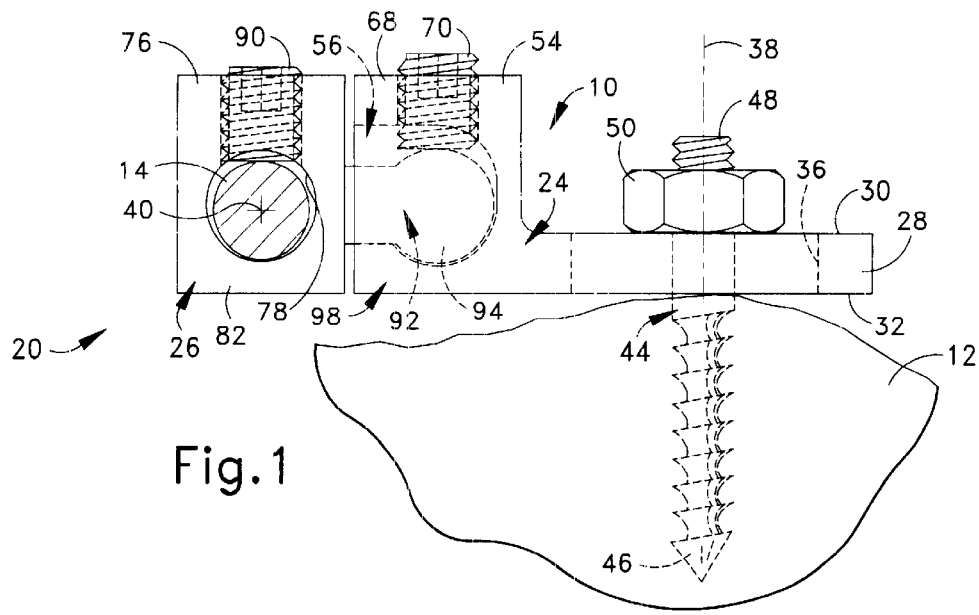
FIG. 1 is an illustration of a first example of a connection assembly in accordance with the present invention, and secured to an associated bone and fixation rod.

An example of a connection assembly 10 in accordance with the present invention is shown in FIG. 1 along with a portion of a bone 12 and an associated fixation rod 14. The connection assembly 10 and associated fixation rod 14 are components of a surgical implant bone fixation arrangement 20 used to maintain bones (e.g., 12) or bone pieces at certain spatial locations. In particular, the arrangement 20 is typically utilized for maintaining vertebrae (e.g., bone 12) of a spinal column in a desired spatial relationship. As such, the arrangement 20 is located adjacent to and connected with anterior portions of vertebrae of the spinal column. However, it is to be noted that the arrangement 20, and in particular the connection assembly 10 of the present invention, may be utilized for other surgical implantation locations and functions. It is to be noted that all of the components of the arrangement 20 may be made of any suitable material, such as surgical stainless steel.

Turning to the connection assembly 10 of FIG. 1, the assembly includes first and second members 24 and 26 as the major components of the assembly. The first member 24 has a planar portion 28 that is intended for location adjacent to, and may contact with, a bone (e.g., bone 12). The planar portion 28 has two major planar surfaces that are parallel to each other. An elongate slot 36 is an opening that extends through the planar portion 28 between the two major surfaces 30, 32. The elongate slot 36 has a through-axis 38 that is transverse to the two major surfaces 30, 32, and an elongation direction (left to right as viewed in FIG. 1) that is generally parallel to the two major surfaces and generally transverse to the through-axis 38. Further, the elongation direction is generally transverse to an elongate axis 40 of the rod 14.

It is to be noted that the orientation relationships such as transverse should be broadly interpreted. Transverse should be interpreted to include perpendicular in orientation and also other obtuse and acute angles. For example, the elongation direction of the slot 36 may be at any of several angles to an axis 40 of the rod 14. Further, it should be noted that the axis 40 of the rod 14 may not be linear along the entire rod length, but that the rod axis may deviate from a straight direction dependent upon curvature, bending, etc. of the rod.

A bone screw fastener 44 extends through the elongate slot 36 and into the bone 12. The bone screw fastener 44 may have any of several configurations. The aspects of such a bone screw fastener 44 include a portion (e.g., 46) that penetrates into the bone 12 to secure the bone screw fastener relative to the bone and also a portion (e.g., 48) that allows the planar portion 28 of the first member 24 to be secured relative to the bone screw fastener. As such, the first member 24 is considered to be a fastener connector of the connection assembly 10.

As shown in the example of FIG. 1, a threaded portion 46 of the bone screw fastener 44 extends into the bone 12. A second, different threaded portion 48 of the bone screw fastener 44 extends at least partially within the elongate slot 36 of the planar portion 28 and receives a threaded nut 50.

Due to the elongation of the slot 36, the first member 24 can be moved, laterally as viewed in FIG. 1, relative to the bone 12 and the bone screw fastener 44 extending therethrough. Upon tightening of the threaded nut 50 onto the mating threaded portion 48 of the bone screw fastener 44, the planar portion 28, and thus the first member 24, are fixed relative to the bone 12. Of course any suitable drive surfaces for the bone screw fastener and/or the one or more nuts may be utilized.

It is to be appreciated the type and use of the bone screw fastener 44 and associated nut 50 are not limitations on the present invention. A different fastener type could be utilized. For example, more than one threaded nut may be utilized, with a threaded nut located on each of the two sides of the planar portion 28. Also, a shoulder assembly may be provided on the bone screw fastener at one side of the planar portion 28 that is opposite to the side against which the threaded nut engages.

A second portion 54 of the first member 24 is referred herein as a socket-block portion. In one example, the two portions (i.e., the planar portion and the socket-block portion) 28, 54 of the first member 24 are integrally formed as a single piece from a single material (e.g., surgical stainless steel). In one example, the first member 24, with the integral two portions 28, 54, are machined from a stock material blank. However, it is possible that the planar portion 28 and the socket-block portion 54 may otherwise be permanently joined (e.g., such as by welding) to be integral.

The socket-block portion 54 is located at one end (left end as viewed in FIG. 1) of the planar portion 28. Specifically, the socket-block portion 54 is located at an end of the planar portion 28 that is along the elongate direction of the slot 36. The exterior surfaces of the socket-block portion 54 are shown to be planar and rectilinear. However, it is to be appreciated that the socket-block portion 54 may have a different configuration (e.g., curved surfaces).

A socket 56 extends into the socket-block portion 54. In the illustrated example, the socket 56 extends into the socket-block portion 54 from a surface 58 of the socket-block portion 54 that is distal from the planar portion 28 of the first member 24. Further, in the illustrated example, the socket 56 extends into the socket-block portion 54 along a direction that is generally parallel to the elongate direction of the slot 36. It is to be appreciated that the socket 56 may have a different orientation relative to the socket-block portion 54. The socket 56 includes an enlarged spherical portion 60 at its furthest interior reach and a throat portion 62 extending from the spherical portion out to an opening of the socket at the surface 58.

Figure 2:
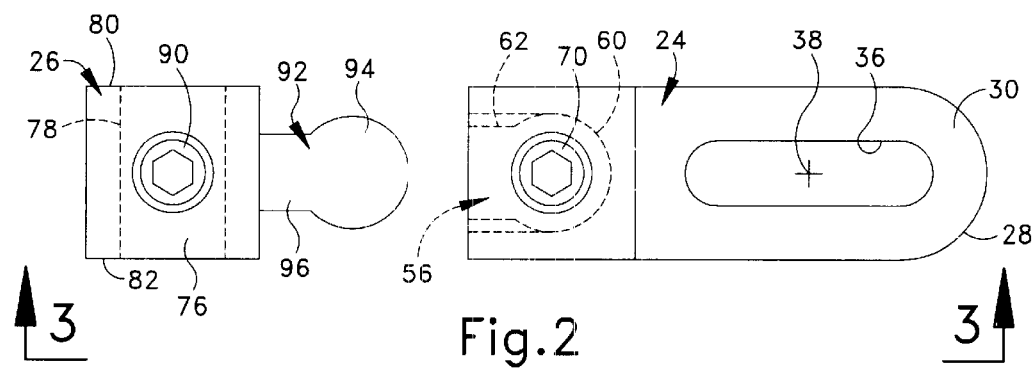
FIG. 2 is an exploded top view of the connection assembly shown in FIG. 1.
Figure 3:
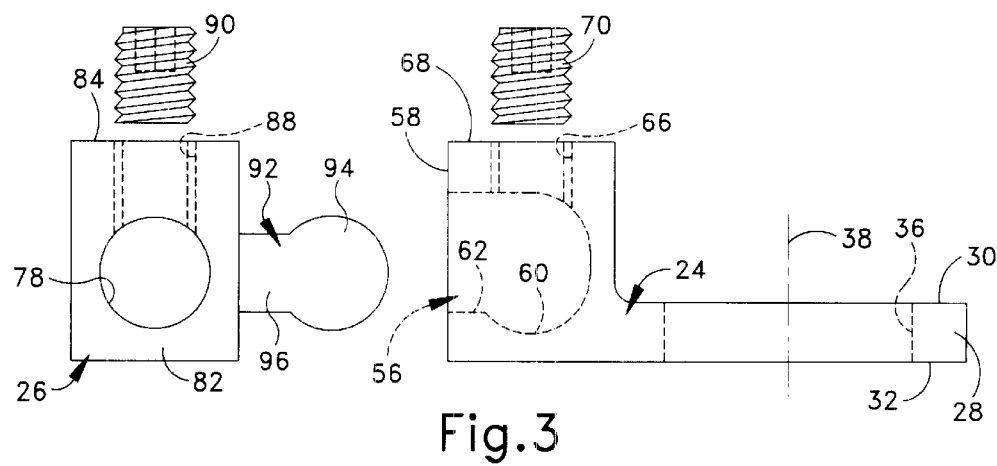
FIG. 3 is a view taken along line 3—3 in FIG. 2.

The throat portion 62 may have a taper as shown in the example of FIGS. 1–3. Specifically, the throat portion 62 has an increasing cross-section area as the throat portion extends from the spherical portion 60. Of course, it is to be appreciated that the throat portion 62 may not be tapered.

A threaded hole 66 extends through the socket-block portion 54 and into the socket 56. In the illustrated example, the threaded hole 66 extends from a surface 68 of the socket-block portion 54 that is perpendicular to the surface 58 through which the socket 56 extends. A threaded set screw 70 is fittingly engaged within the threaded hole 66 to extend at least partially into the socket 56. The set screw 70 has any suitable drive engaging surfaces (e.g., hex head surfaces). The set screw 70 is utilized to secure and fix a portion of the second member 26 within the socket 56, as will be described below.

Turning to the second member 26, the member has a block portion 76 through which a rod hole 78 extends to provide an aperture. The exterior surfaces of the block portion 76 are shown to be planar and rectilinear. However, it is to be appreciated that the block portion 76 may have a different configuration (e.g., curved surfaces). In the illustrated example, the rod hole extends between surfaces 80 and 82, as seen in FIG. 2.

The fixation rod 14 extends through the rod hole 78. In the illustrated example, the rod hole 78 and the rod 14 each have circular cross-sections. Typically, the diameter of the rod hole 78 is slightly greater than the outer diameter of the rod 14 to permit the rod to be moved relative to the block portion 76 through the rod hole.

It is to be appreciated that other constructions and shapes for the rod 14 and the block portion 76 that permit the relative movement are contemplated. Also, it is to be appreciated that other constructions and shapes for the rod 14 and the block portion 76 that provide for fixing the rod relative to the block portion subsequent to such relative movement are contemplated. For example, the rod hole 78 may have a cross section that is asymmetrical, oblong, oval, V-shaped, etc., with a dimension at the portion (e.g., lower) opposite the set screw 90 being such that the rod hole provides an increased wedging action to the rod 14. As a specific example (i.e., an example of an asymmetrical cross section), the rod hole 78 may be provided with two portions that extend the length of the rod hole, with one portion being an upper portion and the other portion being a lower portion. Each of the two portions has a circular cross section, with the radius of the upper portion being greater than the radius of the lower portion. The radius of the upper portion is greater than the radius of the rod 14, and the radius of the lower portion is less (e.g., slightly less) than the radius of the rod. These portions can be thought of as being overlapping holes. The rod 14 can freely move along the upper portion, but when the set screw 90 forces the rod into the lower portion a force or interference fit interconnection is provided.

A threaded hole 88 extends from a surface 84, through the block portion 76, and into the rod hole 78. A threaded set screw 90 is engaged into the threaded hole 88 such that the set screw can extend partially into the rod hole 78 and engage the rod 14 located therein. The set screw 90 wedges the rod 14 against the opposed side of the rod hole 78. As such, the set screw 90 fixes the second member 26 of the connection assembly 10 relative to the rod 14. Accordingly, the second member 26 is considered to be a member connector of the connection assembly 10.

The second member 26 includes a projection portion 92 that extends from the block portion 76. The projection portion 92 includes a ball 94 located at an end of the projection portion distal from the block portion 76. A neck 96 of the projection portion 92 is located intermediate the ball 94 and block portion 76. The neck 96 has a cross-sectional diameter that is less than a maximum diameter of the ball 94.

In one example, the two portions (i.e., the block portion and the projection portion) 76, 92 of the second member 26 are integrally formed as a single piece from a single material (e.g., surgical stainless steel). In one example, the second member 26, with the integral two portions 76, 92, are machined from a stock material blank. However, it is possible that the block portion 76 and the projection portion 92 may otherwise be permanently joined (e.g., such as by welding) to be integral.

The projection portion 92 of the second member 26 extends into the socket 56 of the first member 24. Specifically, the ball 94 is located in the spherical portion 60 of the socket 56, and the neck 96 of the projection portion is located along the throat portion 62 of the socket. The set screw 70 engages the ball 94 upon tightening of the set screw and pushes the ball into the surface defining the spherical portion 60. The throat portion 62 within the socket-block portion 54 is sufficiently large to allow the ball 94 to pass through the throat portion 62 but will cause entrapment of the ball once the ball is engaged by the set screw 70.

It should be appreciated that the ball 94 may be rotated relative to the first member 24 while the ball is within the spherical portion 60 of the socket 56. Specifically, the ball 94 can be moved such that the second member 26 is universally pivotable relative to the first member 24. The taper of the throat portion 62 of the socket 56 permits an increased range of relative motion. As such, the ball 94 and the socket 56 provide a ball and socket joint 98. Further, this ball and socket joint 98 is considered to be one type of a universal pivot interconnection or joint.

Examples of the pivoting movement include upward and downward pivoting movement of the second member 26, with reference to the plane of the FIG. 1 drawing, and pivoting movement of the second portion into and out of the plane of the FIG. 1 drawing. It will be appreciated that the universal pivot movement includes movement in at least two dimensions. The two dimensions of movement are transverse to the direction of elongation of the slot 36. Also, the second member 26 is rotatable relative to the first member 24. Naturally, the movement of the second member 26 is relative to the first member 24. As such, the first member 24 is able to move relative to the second member and the plane of the FIG. 1 drawing is a corollary fashion.

The pivoting movement provides for adjustment of the second member 26, to which the rod 14 is or will be fixed, relative to the first member 24, to which the bone 12 is or will be fixed. Once adjustment at the ball and socket joint 98 is accomplished, the set screw 70 is tightened such that the set screw engages the ball 94 and pushes the ball into the surface defining the spherical portion 60. As such, the ball 94 is entrapped within the socket 56 and is held against motion with respect to the first member 24. Accordingly, the second member 26 is held against motion relative to the first member 24. The ball and socket joint 98 between the first and second members 24 and 26 provide several degrees of freedom for adjustment, followed by a subsequent fixation. This is in addition to the lateral accommodation adjustment provided by the elongate slot 36.

Figures 4, 5:
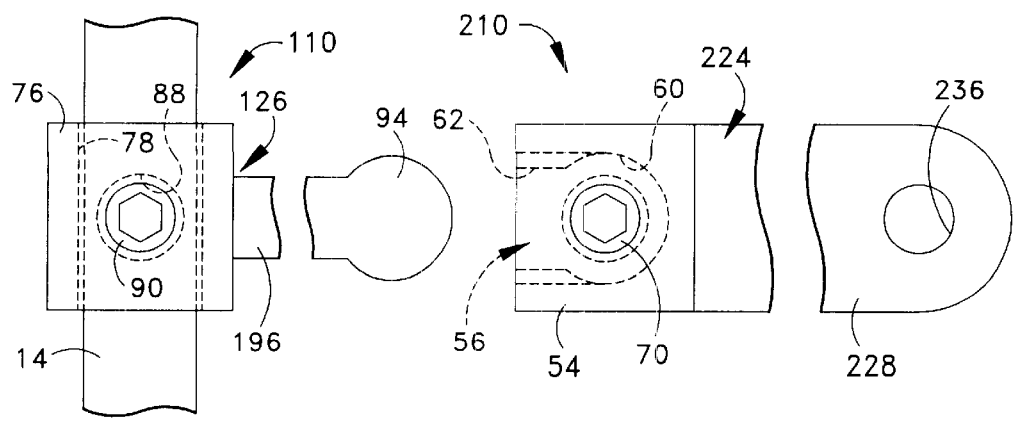
FIG. 4 is a top view of one portion of a second embodiment of a connector assembly in accordance with the present invention along with an associated fixation rod.
FIG. 5 is a top view of one portion of another embodiment of a connection assembly in accordance with the present invention.

Turning again to the aspect of lateral accommodation, the embodiment shown in FIGS. 1–3 shows an example within the present invention in which the bone screw fastener 44 can be secured at any of several locations along the elongate slot 36. However, it is to be appreciated that the embodiment of FIGS. 1–3 is but one example in which lateral adjustment within the present invention can be accomplished. Lateral adjustment, or, more broadly, changes in lateral position can be accomplished by other mechanisms. FIG. 4 illustrates a member 126 of a connection assembly 110 of a second embodiment in which changes in lateral position are possible. The member 126 shown in FIG. 4 is a second member of such other embodiment, which is the member that engages the rod 14. It is to be appreciated that another member (i.e., a first member) of the connection assembly 110 that engages the bone is provided but not shown in FIG. 4. The first member (not shown) may be identical to the first member 24 of the embodiment of FIGS. 1–3.

Many of the structures of the second member 126 of the embodiment of FIG. 4 are effectively identical to the corresponding structures of the second member 26 of the embodiment of FIGS. 1–3. Identical reference numerals are used to identify such effectively identical structures in the embodiment of FIG. 4 and other subsequent embodiments. In many instances, the substantial identical structures are not discussed specifically further herein.

In distinction from the first embodiment (FIGS. 1–3), the second member 126 (second embodiment, FIG. 4) includes a neck 196 of a projection portion 192 that may have a length between the block portion 76 and a ball 194 that is different from the length of the neck 96 shown in the embodiment of FIGS. 1–3. The tear line within FIG. 4 is provided to indicate that the length of the neck 196 may be of any desirable length. It is to be appreciated that the length of the neck 196 can be chosen to provide a desired lateral positioning of the fixation rod 14 relative to the bone (not shown in FIG. 4). Accordingly, the second member 126 within this embodiment could be chosen for neck length to provide desired lateral positioning and/or provide an additional range of lateral positioning beyond the range of positioning provided solely by the elongate slot 36 of the first member 24 (see FIGS. 1–3).

Continuing with the concept of lateral positioning adjustment or variation, attention is directed to FIG. 5. Within FIG. 5, a member 224 of a connection assembly 210 of another embodiment is shown. Specifically, the shown member 224 is a first member of the connection assembly 210. It is to be appreciated that another member (i.e., a second member) of the connection assembly 210 that engages the fixation rod is provided but not shown. The no-show second member may be identical to the second member 26 of the embodiment of FIGS. 1–3 or may be identical to the second member 126 of the embodiment of FIG. 4.

Many of the structures of the first member 224 of the embodiment of FIG. 5 are effectively identical to the corresponding structures of the first member 24 of the embodiment of FIGS. 1–3. Identical reference numerals are used to identify effectively identical structures. The first member 224 shown in FIG. 5 differs from the first member 24 of the embodiment of FIGS. 1–3 in that the first member 224 of FIG. 5 includes a circular hole 236 rather than an elongate slot. As such, a bone screw (not shown in FIG. 5) that extends through the opening of the circular hole 236 can only engage the first member 224 at a single location. However, a planar portion 228 of the first member shown within FIG. 5 has a length that can be chosen. In other words, different lengths of the planar portion 228 are available. This differing length is illustrated by the tear line shown in FIG. 5. As such, in order to achieve lateral adjustment or change of position of the socket-block portion 54, and thus the ball and socket joint and the second member with the affixed rod, a first member 224 having a different length planar portion 228 is selected.

Figure 6:
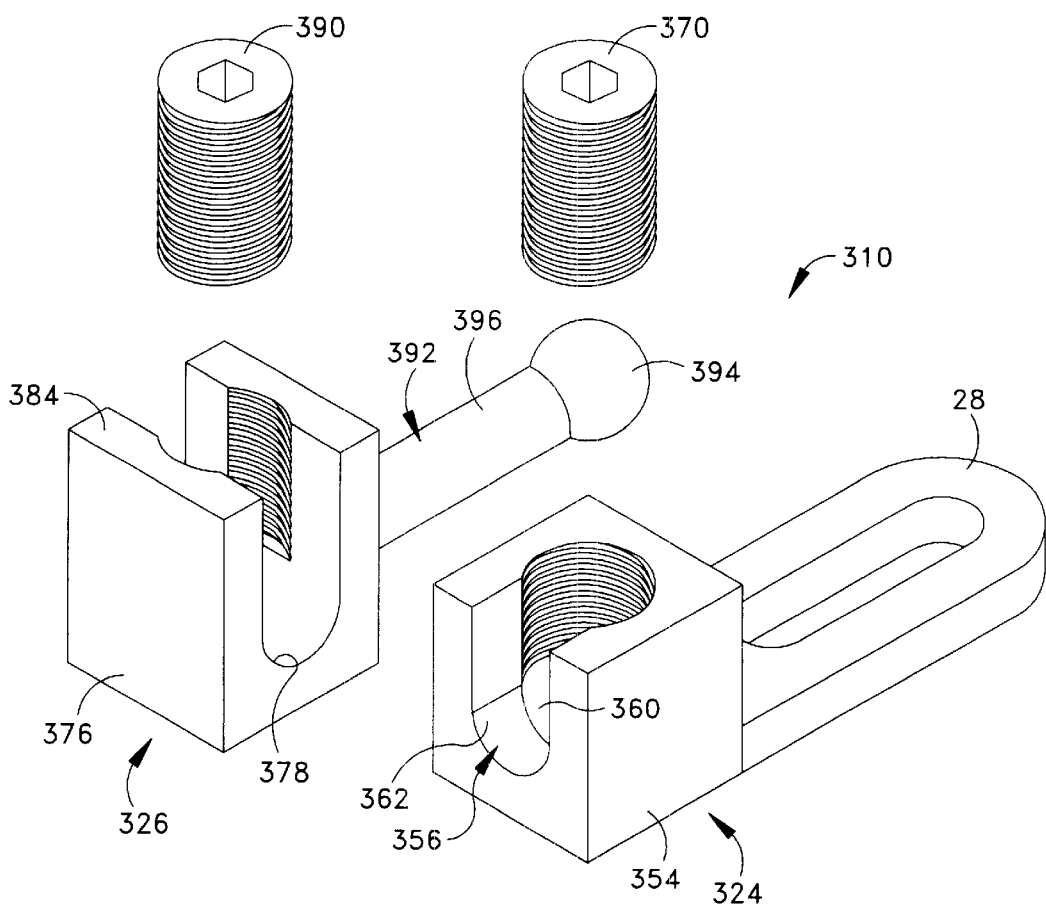
FIG. 6 is an exploded perspective view of another embodiment of a connection assembly in accordance with the present invention.

It is to be appreciated that various other modifications and thus other embodiments within the scope of the present invention are possible. As one example, attention is directed to FIG. 6, which shows first and second members 324 and 326 of a connection assembly 310 along with associated set screws 370 and 390. In the example of FIG. 6, the first member 324 has a planar portion 28 substantially identical to the planar portion 28 of the embodiment of FIGS. 1–3.

A socket-block portion 354 of the embodiment shown in FIG. 6 differs from the socket block portion 54 of the embodiment of FIGS. 1–3. Specifically, a socket of the embodiment of FIG. 6 is provided via a socket slot 356 that extends into the socket-block portion 354 from the same direction that the set screw 370 is brought into engagement with the socket-block portion 354. As shown in FIG. 6, the socket slot 356 includes a portion 360 that terminates at a spherical surface that is large enough to accommodate a ball 394 on a projection portion 392 of the second member 326. The projection portion 392 may be identical to the projection portion 92 of the embodiment shown in FIGS. 1–3, but may differ and is thus identified by a different reference numeral.

The socket slot 356 includes a narrow throat portion 362 that can accommodate a neck 396 of the projection portion 392 on the second member 326. Further, the throat portion 362 accommodates movement of the neck 396 but does not permit extraction of the ball 394 along the throat portion. As such, the projection portion 392 is placed into the socket slot 356 from above as shown in FIG. 6. Once the second member 326 is adjusted relative to the first member 324 by pivoting of the ball 394 within the socket slot 356, the associated set screw 370 is tightened to entrap the ball within the socket slot holding the ball relative to the socket-block portion 354 and fixing the second member 326 in position relative to the first member 324. Typically, the set screw 370 used for the embodiment of FIG. 6 is larger than the set screw 70 of the embodiment of FIGS. 1–3.

The second member 326 of the embodiment shown in FIG. 6 has a modified rod hole as compared to the rod hole 78 shown in the embodiment of FIGS. 1–3. In fact, the rod hole has been modified to be a rod slot 378 extending into a block portion 376 of the second member 326. In the example shown in FIG. 6, the rod slot 378 extends into the block portion 376 from an upper surface 384. With the rod (not shown) located within the rod slot 378, the associated set screw 390 is tightened to engage the rod. This entraps the rod within the second member 326 and fixes the rod relative to the second member. Typically, the set screw 390 used for the embodiment of FIG. 6 is larger than the set screw 90 for the embodiment of FIGS. 1–3.

Figure 7:
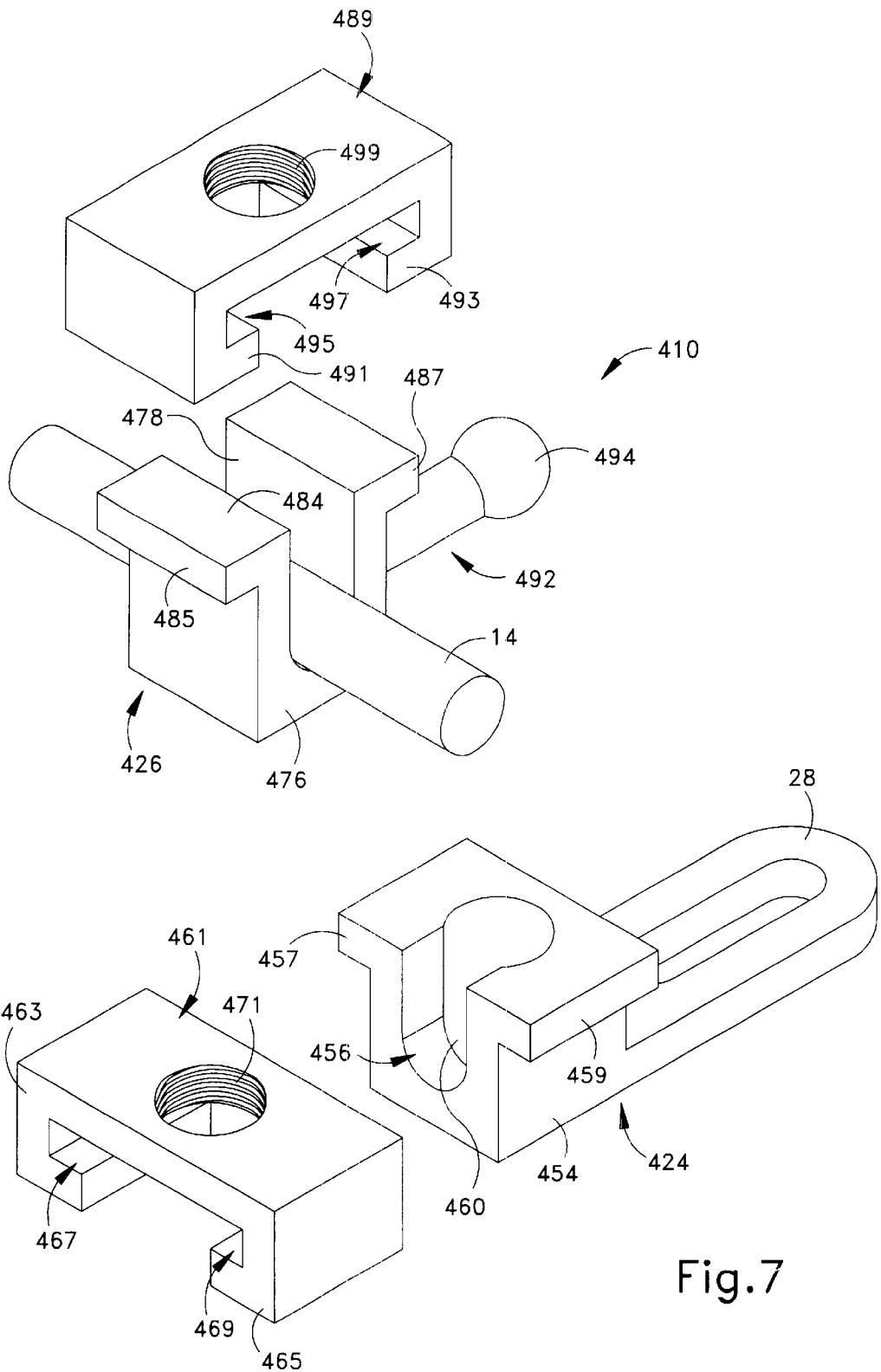
FIG. 7 is an exploded perspective view of another embodiment of a connection assembly in accordance with the present invention, along with an associated fixation rod.

Still further modifications within the scope of the present invention are possible. Another example is shown by the embodiment of a connection assembly 410 (FIG. 7). Within the connection assembly 410, a socket-block portion 454 of a first member 324 has a socket slot 456 that extends downwardly into the socket block portion similar to the embodiment shown in FIG. 6. However, the socket-block portion 454 (FIG. 7) does not include a threaded portion that is engaged by a set screw. Instead, the socket-block portion 454 has two outwardly extending lip projections 457, 459. These projections 457, 459 are located on opposed, upper edges of the socket-block portion 454.

A cap 461 is configured to mate with the projections 457, 459 when the cap is slid onto an upper end of the socket block portion 454. Specifically, the cap 461 has two downwardly and inwardly extending lip portions 463, 465 that provide respective channels 467, 469 within which the outward lip projections 457, 459 are located when the cap is located onto the socket-block portion 454. A threaded set screw hole 471 extends through the cap 461. With the cap 461 located on the socket-block portion 454 of the first member 424, the hole 471 is located above a spherical portion 460 of the socket slot 456 within the socket-block portion 454. A set screw (not shown) threadingly engages the set screw hole 471 and extends into the socket slot 456. The set screw engages a ball 494 on a projection portion 492 of a second member 426 when the ball is located within the socket slot 456. The projection portion 392 may be identical to the projection portion 92 of the embodiment shown in FIGS. 1–3, but may differ and is thus identified by a different reference numeral.

Similar to the previous embodiments, the ball 494 and socket slot 456 provide a universal joint for adjustment. Once adjustment is selected, the associated set screw is tightened to secure the ball 494 within the socket slot 456 and fix the second member 426 relative to the first member 424. In addition, the associated set screw, via force transmitted to the cap 461, will cause a lifting action of the cap against the outward lipped projections 457, 459 on the first member 424. As such, the cap 461, with the carried set screw, are fixed relative to the first member 424.

The second member 426 of the embodiment shown in FIG. 7 has structural features similar to the second member 326 of the embodiment of FIG. 6. Specifically, a rod slot 478

(FIG. 7) extends into a block portion 476 from an upper surface 484. The second member 426 also has structural features similar to the first member 424. Specifically, the block portion 476 includes two outwardly extending lip projections 485, 487. A cap 489 is provided that has two downward and inward extending lips 491, 493 to provide channels 495, 497 for the projections 485, 487. A set screw (not shown) extends through a set screw hole 499 in the cap 489 and into the rod slot 478 and engages the rod 14 located within the rod slot. Upon tightening of the set screw, the rod 14 is fixed relative to the second member 426 and the cap 489 and the carried set screw are fixed relative to the second member 426.

It is to be appreciated that the present invention provides an associated method of connecting a bone engaging fastener to an elongate member, and numerous variations of the method. The broadest aspect of the method is applicable to all of the example embodiments. As such, reference numerals are omitted for method steps that are generic to several example embodiments. Within the method, the fastener connector is connected to the bone engaging fastener. It is noted that the fastener connector has the first fastener connector portion for location adjacent to the bone and has the opening through which the fastener can extend and into the bone. The second fastener connector portion has the part to engage the member connector. The step of connecting the fastener connector includes selecting a distance, to space the second fastener connector portion from the bone engaging fastener, from among a plurality of distance choices, and securing the fastener connector to the bone engaging fastener with the second fastener connector portion at the selected distance from the bone engaging fastener.

The method includes connecting and securing the member connector, which has the portion to connect with the elongate member, to the elongate member. The method includes connecting the fastener connector and the member connector. The fastener connector and the member connector have parts that engage each other to permit relative adjustment movement in at least two dimensions and to secure the member connector relative to the fastener connector subsequent to the adjustment. The step of connecting the fastener connector and the member connector includes relatively adjusting the fastener connector and the member connector in the at least two dimensions and securing the member connector relative to the fastener connector subsequent to the adjustment.

When the method is used in conjunction with the embodiment shown in FIGS. 1–3, 6, or 7, the step of selecting a distance includes selecting a distance along the elongate slot at which to secure the bone engaging fastener. When the method is used in conjunction with the embodiment shown in FIG. 5 the step of selecting a distance includes selecting a fastener connector that has an associated distance between the second fastener connector portion and the hole.

Additional method steps are to be appreciated as the steps relate to structural components and interrelationships. For example, the step of relatively adjusting the fastener connector and the member connector in the at least two dimensions includes adjusting a universal connection between the fastener connector and the member connector. Specifically, the step of adjusting the universal connection between the fastener connector and the member connector includes adjusting the ball and socket connection.

From the above description of the invention, those skilled in the art will perceive improvements, changes and modifications. Such improvements, changes and modifications within the skill the of the art are intended to be covered by the appended claims.

Having described the invention, the following is claimed:

1. A connection assembly for connecting a bone engaging fastener to an elongate member, the assembly including:
   a fastener connector having a slot through which the fastener can extend to secure the fastener connector and fastener together, the slot being elongate to permit securing of the fastener at any of several locations along the slot; and
   a member connector having a portion to connect with the elongate member;
   the fastener connector and the member connector having portions that engage each other to permit relative adjustment movement in at least two dimensions and to secure the member connector relative to the fastener connector subsequent to the adjustment.

2. A connection assembly as set forth in claim 1, wherein the two dimensions of movement are transverse to a direction of elongation of the slot.

3. A connection assembly as set forth in claim 1, wherein the portions of the fastener connector and the member connector that engage each other include a universal joint.

4. A connection assembly as set forth in claim 3, wherein the universal joint includes a ball and socket joint.

5. A connection assembly as set forth in claim 4, wherein a socket of the ball and socket joint in located on the fastener connector and a ball of the ball and socket joint in located on the member connector.

6. A connection assembly as set forth in claim 4, wherein a ball of the ball and socket joint is located on a distal end of a neck of any length.

7. A connection assembly as set forth in claim 4, wherein a socket of the ball and socket joint includes a spherical portion for receiving a ball of the ball and socket joint, and the socket includes a throat portion for prevention of removal of the ball from the spherical portion.

8. A connection assembly as set forth in claim 4, wherein the portions to secure the member connector relative to the fastener connector includes a set screw associated with a socket of the ball and socket joint and engagable with a ball of the ball and socket joint.

9. A connection assembly for connecting a bone engaging fastener to an elongate member, the assembly including:
   a fastener connector having a slot through which the fastener can extend to secure the fastener connector and fastener together, the slot being elongate to permit securing of the fastener at any of several locations along the slot; and
   a member connector having a portion to connect with the elongate member;
   the fastener connector and the member connector having a universal pivot interconnection there between to permit relative universal pivot adjustment movement.

10. A connection assembly as set forth in claim 9, wherein the universal pivot interconnection includes a ball and socket joint.

11. A connection assembly as set forth in claim 10, wherein a ball of the ball and socket joint is located on a distal end of a neck of any length.

12. A connection assembly as set forth in claim 10, wherein a socket of the ball and socket joint includes a spherical portion for receiving a ball of the ball and socket joint, and the socket includes a throat portion that can prevent removal of the ball from the spherical portion.

13. A connection assembly for connecting a bone engaging fastener to an elongate member, the assembly including:

a fastener connector having two integrally formed portions, the first fastener connector portion for location adjacent to the bone and having an opening through which the fastener can extend and into the bone, and the second fastener connector portion having one part of a ball and socket connection; and a member connector having two integrally formed portions, the first member connector portion having another part of the ball and socket connection engaged with the part of the ball and socket connection of the fastener connector, and the second member connector portion having an aperture for receiving the elongate member.

14. A connection assembly as set forth in claim 13, wherein the opening is an elongate slot.

15. A connection assembly as set forth in claim 13, wherein the part of the ball and socket connection of the fastener connector is a socket, and the part of the ball and socket connection of the member connector is a ball.

16. A connection assembly as set forth in claim 13, wherein a ball of the ball and socket joint is located on a distal end of a neck of any length.

17. A connection assembly as set forth in claim 13, wherein a socket of the ball and socket joint includes a spherical portion for receiving a ball of the ball and socket joint, and the socket includes a throat portion that can prevent removal of the ball from the spherical portion.

18. A connection assembly as set forth in claim 13, wherein the opening through the fastener connector is located at any length from the second fastener connector portion having the one part of a ball and socket connection.

19. A method of connecting a bone engaging fastener to an elongate member, the method including:

connecting a fastener connector to the bone engaging fastener, the fastener connector having a first fastener connector portion for location adjacent to the bone and having an opening through which the fastener can extend and into the bone, and a second fastener connector portion having a part to engage a member connector, the step of connecting the fastener connector includes selecting a distance, to space the second fastener connector portion from the bone engaging fastener, from among a plurality of distance choices, and securing the fastener connector to the bone engaging fastener with the second fastener connector portion at the selected distance from the bone engaging fastener;

connecting and securing a member connector, which has a portion to connect with the elongate member, to the elongate member; and connecting the fastener connector and the member connector, the fastener connector and the member connector have parts that engage each other to permit relative adjustment movement in at least two dimensions and to secure the member connector relative to the fastener connector subsequent to the adjustment, the step of connecting the fastener connector and the member connector includes relatively adjusting the fastener connector and the member connector in the at least two dimensions and securing the member connector relative to the fastener connector subsequent to the adjustment.

20. A method as set forth in claim 19, wherein the step of selecting a distance includes selecting a distance along an elongate slot at which to secure the bone engaging fastener.

21. A method as set forth in claim 19, wherein the step of selecting a distance includes selecting a fastener connector that has an associated distance between the second fastener connector portion and the hole.

22. A method as set forth in claim 19, wherein the step of relatively adjusting the fastener connector and the member connector in the at least two dimensions includes adjusting a universal connection between the fastener connector and the member connector.

23. A method as set forth in claim 22, wherein the step of adjusting a universal connection between the fastener connector and the member connector includes adjusting a ball and socket connection.

\* \* \* \* \*